US011932557B2

(12) United States Patent
Shi et al.

(10) Patent No.: US 11,932,557 B2
(45) Date of Patent: Mar. 19, 2024

(54) DETECTION AND EXTRACTION OF PLASTIC CONTAMINANTS WITHIN WATER USING HYDROPHOBIC DEEP EUTECTIC SOLVENTS

(71) Applicant: University of Kentucky Research Foundation, Lexington, KY (US)

(72) Inventors: Jian Shi, Lexington, KY (US); Wenqi Li, Lexington, KY (US); Jameson Hunter, Lexington, KY (US); Yuxuan Zhang, Lexington, KY (US); Qing Shao, Lexington, KY (US)

(73) Assignee: UNIVERSITY OF KENTUCKY RESEARCH FOUNDATION, Lexington, KY (US)

(*) Notice: Subject to any disclaimer, the term of this patent is extended or adjusted under 35 U.S.C. 154(b) by 169 days.

(21) Appl. No.: 17/362,515

(22) Filed: Jun. 29, 2021

(65) Prior Publication Data

US 2021/0403346 A1    Dec. 30, 2021

Related U.S. Application Data

(60) Provisional application No. 63/046,226, filed on Jun. 30, 2020.

(51) Int. Cl.
*C02F 1/26* (2023.01)
*B01D 11/04* (2006.01)
(Continued)

(52) U.S. Cl.
CPC ............ *C02F 1/26* (2013.01); *B01D 11/0492* (2013.01); *G01N 21/94* (2013.01); *G01N 33/18* (2013.01); *C02F 2101/34* (2013.01)

(58) Field of Classification Search
CPC .... C02F 1/26; C02F 2101/34; C02F 2101/30; B01D 11/0492; B01D 11/04; G01N 21/94; G01N 33/18; G01N 1/4055; G01N 2001/4061; G01N 21/25; G01N 21/31; G01N 25/00; G01N 25/08; G01N 25/14; G01N 25/48; G01N 2021/258; G01N 33/1826; C07C 39/02; C07C 39/08;
(Continued)

(56) References Cited

U.S. PATENT DOCUMENTS 8,541,556 B1    9/2013  Gu et al.
8,759,049 B2    6/2014  Pigeau et al.
(Continued)

FOREIGN PATENT DOCUMENTS

CA          3093197 A1  *  9/2012    ............... G01N 1/40
CA          3039880 C   *  4/2020    ............... G01N 1/44
(Continued)

OTHER PUBLICATIONS

English Translation of Zhao Publication CN106745443B, published Feb. 2018. (Year: 2018).*
(Continued)

*Primary Examiner* — Joseph W Drodge
(74) *Attorney, Agent, or Firm* — Stites & Harbison, PLLC; Gary N. Stewart; Mandy Wilson Decker

(57) ABSTRACT

Methods for detecting and extracting plastic contaminants within a water sample, which involve introducing the water sample to a hydrophobic deep eutectic solvent, are provided.

22 Claims, 8 Drawing Sheets

(51) Int. Cl.
  *G01N 21/94* (2006.01)
  *G01N 33/18* (2006.01)
  *C02F 101/34* (2006.01)
(58) Field of Classification Search
  CPC ......... C07C 39/10; C07C 39/11; C07C 47/56; C07C 47/565; C07C 47/57; C07C 59/48; G01J 3/00; G01J 3/28; G01J 3/42; G01J 3/44
  See application file for complete search history.

(56) References Cited

U.S. PATENT DOCUMENTS

| | | | |
|---|---|---|---|
| 8,835,140 B2 | 9/2014 | Fernholz et al. | |
| 8,951,960 B2 | 2/2015 | Wiatr et al. | |
| 9,775,347 B2 | 10/2017 | Zhang | |
| 9,790,520 B2 | 10/2017 | Semenza et al. | |
| 10,723,859 B2 * | 7/2020 | Shi | C08J 11/16 |
| 2003/0055007 A1 | 3/2003 | Sakuma | |
| 2012/0207886 A1 | 8/2012 | Shulevitz et al. | |
| 2013/0082003 A1 * | 4/2013 | Bajpayee | B01D 11/0488 210/695 |
| 2014/0045226 A1 | 2/2014 | Wicking et al. | |
| 2015/0118726 A1 | 4/2015 | Wiatr et al. | |
| 2019/0119704 A1 | 4/2019 | Fernholz et al. | |
| 2019/0383720 A1 * | 12/2019 | Savoy | G01N 33/18 |
| 2020/0062681 A1 | 2/2020 | Singh et al. | |

FOREIGN PATENT DOCUMENTS

| | | | | |
|---|---|---|---|---|
| CN | 106745443 B * | 2/2018 | | G01N 1/4055 |
| CN | 109187096 A * | 1/2019 | | G01N 1/14 |
| CN | 111474132 B * | 9/2021 | | G01N 21/3577 |
| JP | 2000191520 A | 7/2000 | | |
| WO | WO 2009026706 A | 3/2009 | | |
| WO | WO2017013438 A1 | 1/2019 | | |
| WO | WO 2019083831 A1 | 5/2019 | | |
| WO | WO 2019121147 A1 | 6/2019 | | |
| WO | WO2019171312 A1 * | 9/2019 | | G01N 1/40 |
| WO | WO 2020002008 A1 | 1/2020 | | |

OTHER PUBLICATIONS

Makos et al, "Hydrophobic Deep Eutectic Solvents in Microextraction Techniques—A Review", Published Article in Microchemical Journal—Oct. 2019. (Year: 2019).*
Qu et al, "Synthesis and Characterization of Deep Eutectic Solvents (five hydrophilic and three hydrophobic), and hydrophobic application for microextraction of environmental water samples", Published in Analytical and Bioanalytical Chemistry, 2019, vol. 411, pp. 7489-7498. (Year: 2019).*
Paiva et al, "Natural Deep Eutectic Solvents-Solvents for the 21st Century", Published in American Chemical Society Sustainable Chemical Engineering, vol. 2, pp. 1063-1071. (Year: 2014).*
David K. A. Barnes, "Accumulation and fragmentation of plastic debris in global environments", Philosophical Transactions of the Royal Society B., published Jul. 27, 2009. (Year: 2009).*
National Science Foundation (NSF) 20-050, Dear Colleague Letter: Critical Aspects of Sustainability (CAS): Micro- and Nanoplastics (MNP), published Mar. 2020. (Year: 2020).*
English Translation of Xu et al patent publication CN209187096A, published Jan. 2019. (Year: 2019).*
English Translation of Jiang et al patent publication CN111474132B, published Sep. 2021. (Year: 2021).*
Dwamena, Amos K., Recent Advances in Hydrophobic Deep Eutectic Solvents for Extraction, Separations 2019, 6, 9; pp. 1-15.
Gilmore, et al., Hydrophobic Deep Eutectic Solvents Incorporating Trioctylphosphine Oxide: Advanced Liquid Extractants, ACS Sustainable Chem. Eng. 2018, 6, 17323-17332.
Kim, et al., Supplemental Material, iomass Pretreatment using Deep Eutectic Solvent from Lignin derived Phenols, 2018, Electronic Supplementary Material (ESI) for Green Chemistry, pp. 1-5, available at http://www.rsc.org/suppdata/c7/gc/c7gc03029k/c7gc03029k1.pdf (retrieved Jan. 4, 2022).
Kim, et al., Biomass Pretreatment using Deep Eutectic Solvent from Lignin Derived Phenols, 2018, Green Chemistry, pp. 1-8, available at https://www.researchgate.net/publication/322345426_Biomass_Pretreatment_using_Deep_Eutectic_Solvent_from_Lignin_derived_Phenols (retrieved Jan. 4, 2022).
Cao, J.; Yang, M.; Cao, F.; Wang, J.; Su, E., Well-Designed Hydrophobic Deep Eutectic Solvents as Green and Efficient Media for the Extraction of Artemisinin from Artemisia annua Leaves. ACS Sustainable Chemistry & Engineering 2017, 5 (4), 3270-3278.
Florindo, C.; Branco, L. C.; Marrucho, I. M., Development of hydrophobic deep eutectic solvents for extraction of pesticides from aqueous environments. Fluid Phase Equilibria 2017, 448, 135-142.
Mintenig, S. M.; Bäuerlein, P. S.; Koelmans, A. A.; Dekker, S. C.; van Wezel, A. P., Closing the gap between small and smaller: towards a framework to analyse nano- and microplastics in aqueous environmental samples. Environmental Science: Nano 2018, 5 (7), 1640-1649.
Nguyen, B.; Claveau-Mallet, D.; Hernandez, L. M.; Xu, E. G.; Farner, J. M.; Tufenkji, N., Separation and Analysis of Microplastics and Nanoplastics in Complex Environmental Samples. Accounts of Chemical Research 2019, 52 (4), 858-866.
Van Osch, D. J. G. P.; Dietz, C. H. J. T.; van Spronsen, J.; Kroon, M. C.; Gallucci, F.; van Sint Annaland, M.; Tuinier, R., A Search for Natural Hydrophobic Deep Eutectic Solvents Based on Natural Components. ACS Sustainable Chemistry & Engineering 2019, 7 (3), 2933-2942.
Van Osch, D. J. G. P.; Zubeir, L. F.; van den Bruinhorst, A.; Rocha, M. A. A.; Kroon, M. C., Hydrophobic deep eutectic solvents as water-immiscible extractants. Green Chemistry 2015, 17 (9), 4518-4521.
Li, et al., Hydrophobic deep eutectic solvents as extractants for the determination of bisphenols from food-contacted plastics by high performance liquid chromatography with fluorescence detection, Journal of Chromatography A, 2020.
Dodge, L. A. (2018). Fractionation of Lignin Derived Compounds From Thermochemically Processed Lignin Towards Antimicrobial Properties. (Year: 2018).
Sanchez-Maldonado, A. F., Schieber, A., & Ganzle, M. G. (2011). Structure-function relationships of the antibacterial activity of phenolic acids and their metabolism by lactic acid bacteria. Journal of applied microbiology, 111 (5), 1176-1184. (Year: 2011).
Espinoza-Acosta, J. L., Torres-Chavez, P. I., Ramfrez-Wong, B., Lopez-Saiz, C. M., & Montano-Leyva, B. (2016). Antioxidant, antimicrobial, and antimutagenic properties of technical lignins and their applications. Bio Resources, 11(2), 5452-5481. (Year: 2016.
Srinivasulu, Cheemanapalli, et al. "Syringic acid (SA)—a review of its occurrence, biosynthesis, pharmacological and industrial importance." Biomedicine & Pharmacotherapy 108 (2018): 547-557. (Year: 2018).
Suzuki, H., Mori, R., Kato, M., & Shimizu, M. (2022). Biochemical characterization of hydroquinone hydroxylase from Phanerochaete chrysosporium. Journal of Bioscience and Bioengineering. (Year: 2022).
Salvachua, D., Katahira, R., Cleveland, N. S., Khanna, P., Resch, M. G., Black, B. A., ... & Beckham, G. T. (2016). Lignin depolymerization by fungal secretomes and a microbial sink. Green Chemistry, 18(22), 6046-6062. (Year: 2016).
(NIST)National Institute of Standards and Technology. (2021). Benzoic acid, 4-hydroxy-3,5-dimethoxy. Benzoic acid, 4-hydroxy-3,5-dimethoxy—Retrieved on Dec. 14, 2022 from(https://webbook.nist.gov/cgi/inchi/InChl%3D1S/C9H10O5/c1-13-6-3-5(9(11)12)4-7(14-2)8 (6)1 0/h3-4%2C10H%2C1-2H3%2C(H%2C11 %2C12) (Year: 2021).
Harris, et al., Natural Antibacterial Agents from Arid-region Pretreated Lignocellulosic Biomasses and extracts for the Control of Lactic Acid Bacteria in Yeast Fermentation, 2018.
Alzagameen et al., Antimicrobial Activity of Lignin and Lignin-Derived Cellulose and Chitosan Composites Against Selected Pathogenic and Spoilage Microorganisms, 2019.

(56) References Cited

OTHER PUBLICATIONS

Yang et al., Effect of Cellulose and Lignin on Disintegration, Antimicrobial and Antioxidant Properties of PLA Active Films, 2016.

Garcia, et al., Antioxidant and Biocide Behaviour of Lignin Fractions from Apple Tree Pruning Residues, 2017.

Gu et al., Physiological Mechanism of Improved Tolerance of *Saccharomyces cerevisiae* to Lignin-Derived Phenolic Acids in Lignocellulosic Ethanol Fermentation by Short-Term Adaptation, 2019.

Chang et al., Use of Sulfite and Hydrogen Peroxide to Control Bacterial Contamination in Ethanol Fermentation, 1997.

Van der Pol et al., Identifying Inhibitory Effects of Lignocellulosic By-products on Growth of Lactic Acid Producing Micro-organisms using a Rapid Small-Scale Screening Method, 2016.

Bischoff, et al., Modeling Bacterial Contamination of Fuel Ethanol Fermentation, Biotechnology and Bioengineering, vol. 103, No. 1, May 1, 2009, pp. 117-122.

Ma, R., et al., Peracetic Acid Depolymerization of Biorefinery Lignin for Production of Selective Monomeric Phenolic Compounds. Chemistry—A European Journal, 2016. 22(31): p. 10884-10891.

USPTO, Non-Final Office Action for U.S. Appl. No. 17/219,111 dated Dec. 28, 2022.

Reimonn, G., Lu, T., Gandhi, N. & Chen, W.-T. Review of Microplastic Pollution in the Environment and Emerging Recycling Solutions. Journal of Renewable Materials 7, 1251-1268 (2019).

Mao, Y., Li, H., Huangfu, X., Liu, Y. & He, Q. Nanoplastics Display Strong Stability in Aqueous Environments: Insights from Aggregation Behaviour and Theoretical Calculations. Environmental Pollution 258, 113760 (2020).

Schwaferts, C., Niessner, R., Elsner, M. & Ivleva, N. P. Methods for the Analysis of Submicrometer-and Nanoplastic Particles in the Environment. TrAC Trends in Analytical Chemistry 112, 52-65 (2019).

Shelton, L. R. & Capel, P. D. Guidelines for Collecting and Processing Samples of Stream Bed Sediment for Analysis of Trace elements and Organic contaminants for the National Water-Quality Assessment Program. vol. 94 (US Geological Survey, 1994).

Makos et al., "Suplementary Material for Hydrophobic Deep Eutectic Solvents in Microextraction Techniques—A Review" available at https://view.officeapps.live.com/op/view.aspx?src=https%3A%2F%2Fars.els-cdn.com%2Fcontent%2Fimage%2F1-s2.0-S0026265X19329352-mmc1.docx&wdOrigin=BROWSELINK (retrieved Oct. 13, 2023).

* cited by examiner

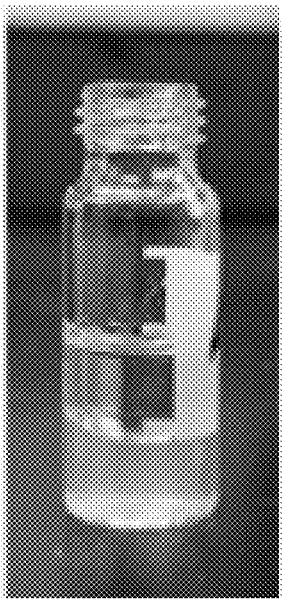
FIG. 5A  FIG. 5B  FIG. 5C  FIG. 5D
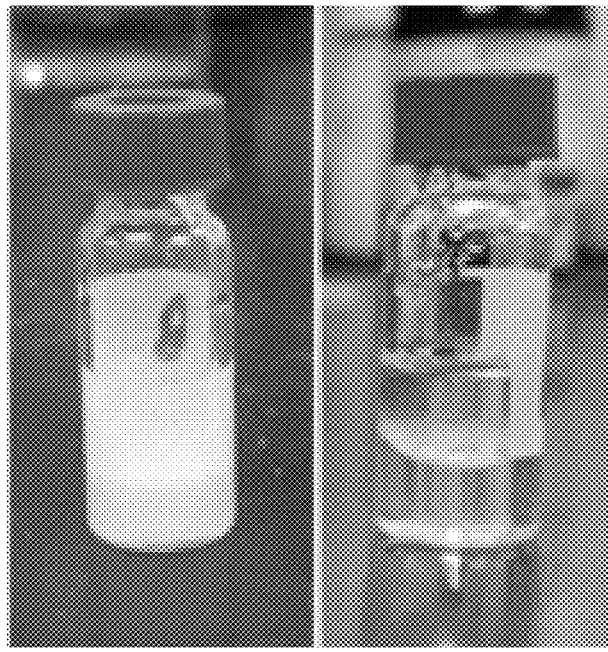
FIG. 6A  FIG. 6B

DETECTION AND EXTRACTION OF PLASTIC CONTAMINANTS WITHIN WATER USING HYDROPHOBIC DEEP EUTECTIC SOLVENTS

RELATED APPLICATIONS

This application claims the benefit of U.S. Provisional Patent Application Ser. No. 63/046,226, filed Jun. 30, 2020, the entire disclosure of which is incorporated herein by this reference.

GOVERNMENT INTEREST

This invention was made with government support under grant number 1018315 awarded by the United States Department of Agriculture (USDA) and grant numbers 1632854 and 1929122 awarded by the National Science Foundation (NSF). The government has certain rights in the invention.

TECHNICAL FIELD

The presently-disclosed subject matter generally relates to the detection and extraction of contaminants within a water sample. In particular, the presently-disclosed subject matter relates to methods for detecting and extracting plastic contaminants within a water sample, which involve introducing the water sample to a hydrophobic deep eutectic solvent.

BACKGROUND

Long-time human activities have led to the widespread deposit of plastic debris into the global aqueous system. Accumulation of micro- and nano-scale plastic particles (i.e., "microplastics" and "nanoplastics," respectively) is the subject of increasing concern as their small size make them hard to remediate using traditional methods. Nanoplastics and microplastics refer to, nanoscale and microscale plastic particles, respectively, composed of organic polymers, such as polystyrene, polyethylene, polypropylene, and polyethylene terephthalate (PET). Nanoplastics and microplastics can be generated through various paths, such as through the mechanical and chemical degradation of plastic wastes widely used for personal and industrial activities. Prior research has identified the presence of nanoplastics within various aqueous systems, including seawater and drinking water. The small size of nanoplastics could make them impact the ecosystem differently from the micro- and macro-plastics. With sizes similar or even smaller than a cell, nanoplastics can penetrate the natural barriers of plants, animals, and humans and thus affect the biological functions of the same. Although the interaction between nanoplastics and ecosystems and the mode of action are still an active area of research, recent studies have revealed that nanoplastics can potentially change the metabolism of human lung cells and significantly decrease the rate of fertilization success of oysters. To date, however, the detection and quantification of nanoplastics within contaminated water samples remains challenging due to the difficulty in collecting nanoplastics from water.

Accordingly, there is a need for additional methods for detecting and extracting plastic contaminants within water samples.

SUMMARY

The presently-disclosed subject matter meets some or all of the above-identified needs, as will become evident of those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes methods and compositions for use in the detection and extraction of plastic contaminants within a water sample.

In some embodiments of the presently-disclosed subject matter, a method is provided for detecting plastic contaminants within a water sample using a hydrophobic deep eutectic solvent (DES), which involves introducing a water sample to the hydrophobic DES; and examining the hydrophobic DES for plastic contaminant enrichment (i.e., the presence of plastic contaminants within the hydrophobic DES) after a period of interaction with the water sample. In some embodiments of the method for detecting plastic contaminants within the water sample, the water sample is introduced to the hydrophobic DES by mixing the water sample with the deep eutectic solvent to form a mixture, and then examining the hydrophobic DES for plastic contaminant enrichment following phase separation between the hydrophobic DES and an aqueous portion of the mixture. In some embodiments, the hydrophobic DES is mixed with the water sample in a volume to volume ratio from about 1:10 to about 1:1. In some embodiments, the hydrophobic DES may be examined for contaminant enrichment via at least one of microscopy, spectrophotometry, and thermogravimetric analysis. In some embodiments, the hydrophobic DES may be examined for plastic contaminant enrichment by examining the optical density of the aqueous portion of the mixture.

In some embodiments of the presently-disclosed subject matter, a method for extracting plastic contaminants within a water sample is provided, which involves introducing the water sample to a hydrophobic DES for a period of time sufficient to extract at least some of the plastic contaminants from the water sample. In some embodiments, introducing the water sample to the hydrophobic DES includes mixing the water sample with the hydrophobic DES for a period sufficient to extract at least 60% of the plastic contaminants from the water sample. In some embodiments, introducing the water sample to the hydrophobic DES includes mixing the water sample with the hydrophobic DES for a period sufficient to extract at least 70% of the plastic contaminants from the water sample. In some embodiments, introducing the water sample to the hydrophobic DES includes mixing the water sample with the hydrophobic DES for a period sufficient to extract at least 80% of the plastic contaminants from the water sample.

In some embodiments, the water sample within the methods for plastic contaminant detection and extraction provided herein is freshwater. In some embodiments, the water sample is salty water. In some embodiments the water sample is contaminated with at least one of nanoplastics and microplastics. In some embodiments, the water sample is contaminated with polyethylene terephthalate (PET). In some embodiments, the water sample is contaminated with polystyrene (PS). In some embodiments, the water sample is contaminated with polypropylene (PP). In some embodiments, the water sample is contaminated with polyethylene (PE). In some embodiments, the water sample is contaminated with polylactic acid (PLA). In some embodiments, the water sample is contaminated with polybutylene succinate (PBS). In some embodiments, the water sample is contaminated with polyhydroxyalkanoate (PHA). In some embodiments, the water sample is contaminated with a mixture of PET and/or PS and/or PP and/or PE and/or PLA and/or PBS and/or PHA plastic particles.

Various hydrophobic DES compositions, each of which may be utilized in the plastic contaminant detection and extraction methods noted above, are also provided. In some embodiments, the hydrophobic DES includes a hydrogen bond acceptor and a hydrogen bond donor mixed in a molar ratio of about 0.1 to about 10 of hydrogen bond acceptor (HBA) to about 1 of hydrogen bond donor (HBD). In some embodiments, the HBA of the hydrophobic DES is selected from one of decanoic acid and thymol. In some embodiments, the HBD of the hydrophobic DES is selected from one of lidocaine and menthol. In some embodiments the hydrophobic DES includes decanoic acid and menthol mixed in a molar ratio of about 1:1 or about 1:2. In some embodiments, the hydrophobic DES includes thymol and menthol mixed in a molar ratio of about 1:1 or about 2:1.

Further features and advantages of the presently-disclosed subject matter will become evident to those of ordinary skill in the art after a study of the description, figures, and non-limiting examples in this document.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein:

FIGS. 5A-5D are images of an aqueous solution of freshwater water sample contaminated with PET nanoplastic particles alone and in combination with a hydrophobic DES comprising decanoic acid and menthol at a 1:1 molar ratio (Dea:Men (1:1) DES). (A) Freshwater water sample contaminated with PET nanoplastic particles alone. (B) Contaminated freshwater water sample in combination with Dea:Men (1:1) DES before mixing. (C) Mixture (1:1 v/v) of contaminated freshwater water sample and Dea:Men (1:1) DES before phase separation. (D) Mixture (1:1 v/v) of freshwater water sample and Dea:Men (1:1) DES after phase separation.

FIGS. 6A-6B are images of a freshwater water sample contaminated with PET nanoplastic particles in combination with a hydrophobic DES comprising thymol and menthol at a 1:1 molar ratio (Thy:Men (1:1) DES). (A) Mixture (1:1 v/v) of contaminated freshwater water sample and Thy:Men (1:1) DES before phase separation. (B) Mixture (1:1 v/v) of freshwater water sample and Thy:Men (1:1) after phase separation.

DESCRIPTION OF EXEMPLARY EMBODIMENTS

Figure 1:
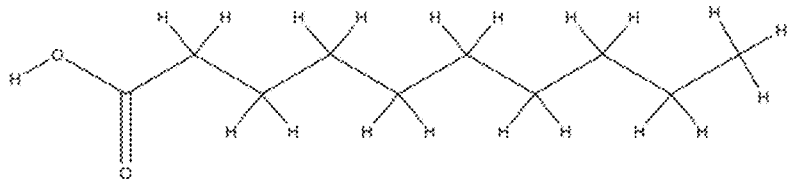
FIG. 1 is a table showing the formula for eight hydrophobic DES compositions that may be used in the detection and extraction of plastic contaminants within a water sample, with molar ratios of the respective organic molecules of such compounds represented in parentheses.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes a method for detecting plastic contaminants within a water sample using a hydrophobic deep eutectic solvent (DES). In the detection method, the presence of plastic contaminants within a water sample is detected by examining the hydrophobic DES for plastic contaminant enrichment (i.e., the presence of plastic contaminants within the hydrophobic DES) following a period of interaction with the water sample. In this regard, the plastic contaminant detection method of the present disclosure generally includes first introducing a hydrophobic DES to a water sample, which may be contaminated with plastic contaminants (e.g., microplastics and/or nanoplastics), and then subsequently examining the hydrophobic DES for plastic contaminant enrichment, with enrichment of the hydrophobic DES indicating contamination of the water sample.

In some embodiments, following interaction with the water sample, the hydrophobic DES may be examined for plastic contaminant enrichment by way of visual examination. For example, in some embodiments, the hydrophobic DES may be determined to be enriched with plastic contaminants upon observing an increase in the opaqueness of the hydrophobic DES following interaction with the water sample. Additionally or alternatively, in some embodiments, the hydrophobic DES may be examined for plastic contaminant enrichment using microscopic, spectrophotometric, and/or thermogravimetric (thermogravimetric analysis) methods. In some embodiments, the hydrophobic DES may be examined using confocal microscopy, Fourier-transform infrared spectroscopy, Raman spectroscopy, and gas chromatography-mass spectrometry, or combinations thereof. In some embodiments, examination of the hydrophobic DES may include quantifying the number of plastic contaminants within the enriched hydrophobic DES. In some embodiments, the number of plastic contaminants within the enriched hydrophobic DES may, in turn, be utilized to quantify the plastic contaminants within the water sample. In some embodiments, the hydrophobic DES may be examined for plastic contaminant enrichment by examining the optical density of the aqueous portion of the mixture.

In some embodiments, the hydrophobic DES is first introduced to the water sample by mixing the hydrophobic DES with the water sample to form a mixture, and then examined for plastic contaminant enrichment following phase separation between the hydrophobic DES and an aqueous portion of the mixture. In some embodiments, the hydrophobic DES is mixed with the water sample at a hydrophobic DES volume to water sample volume ratio ranging from about 1:1 v/v to about 1:10 v/v. Mixing of the water sample and the hydrophobic DES can be performed by way of vortex, agitation, decanting, crossflow, or any other suitable means of mixing, as would be known to one of skill in the art. In some embodiments, the mixture may be centrifuged to further promote phase separation between the hydrophobic DES composition and the aqueous portion of the mixture.

As the DES is hydrophobic, it is nonpolar and thus immiscible with the aqueous portion of the mixture. Thus, unlike traditional deep eutectic solvents, which are water-miscible, the hydrophobic DES does not have the potential to pollute the aqueous system in which it is introduced. Rather, due to the aversion of the hydrophobic DES to water and its affinity to nonpolar organic compounds within the water sample, plastic contaminants within the mixture are extracted from the aqueous portion and recovered in the hydrophobic DES phase of the mixture following phase separation (FIGS. 5D, 6B, 7, and 8), thus leaving an aqueous portion with reduced plastic particle contamination. In this way, the hydrophobic DES may thus be used to extract plastic contaminants from, and thus reduce contamination of, a water sample.

Figure 12:
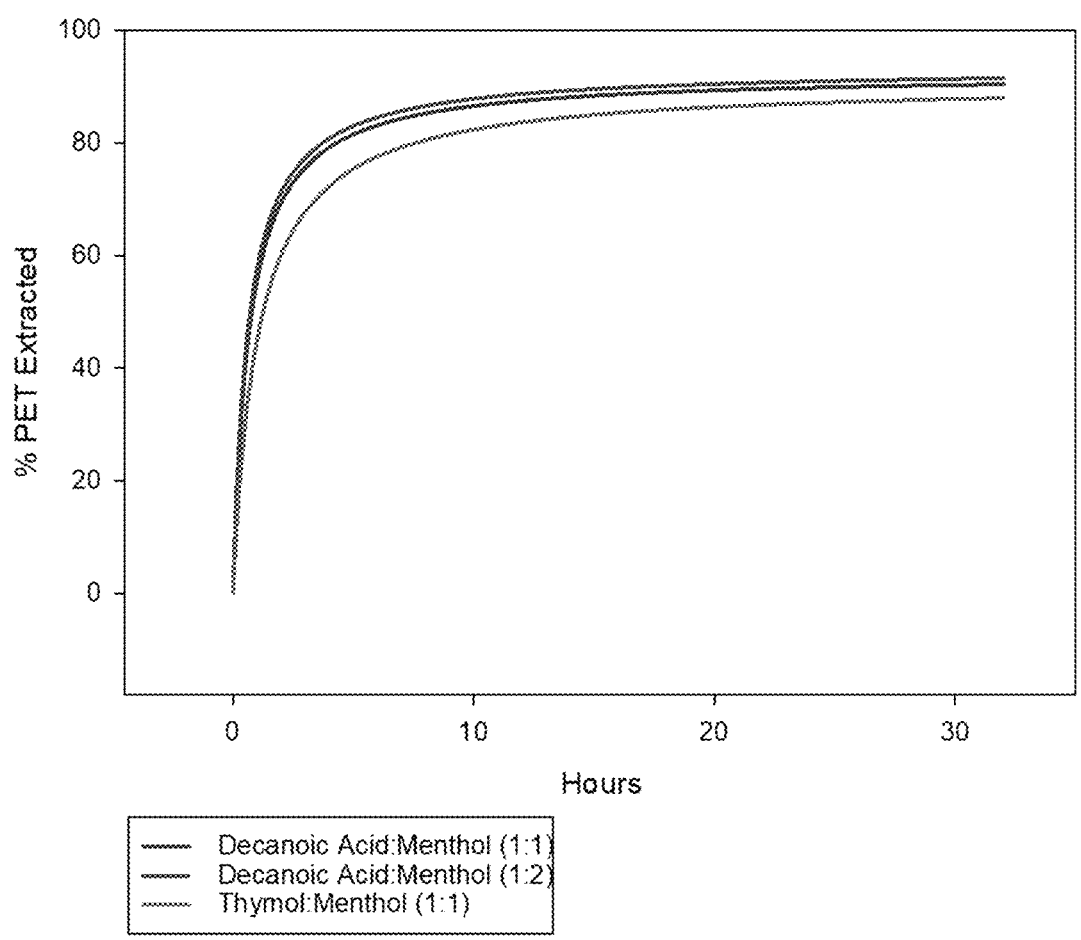
FIG. 12 is a graph showing the percent of PET extracted from a freshwater sample with a concentration of 1 mg/mL of plastic contaminants over a period of 32 hours with constant stirring using Dea:Men (1:1) DES; Dea: Men (1:2) DES; and Thy:Men (1:1) at 1:1 v/v DES to water ratio.

Accordingly, in another aspect, the presently-disclosed subject matter also includes a method for extracting plastic contaminants from a water sample contaminated with plastic contaminants. In some embodiments, the water sample and hydrophobic DES are mixed for a period of interaction sufficient to extract at least 10% of plastic contaminants from the water sample (FIG. 12). In some embodiments, the water sample and hydrophobic DES are mixed for a period of interaction sufficient to extract at least 20% of plastic contaminants from the water sample (FIG. 12). In some embodiments, the water sample and hydrophobic DES are mixed for a period of interaction sufficient to extract at least 30% of plastic contaminants from the water sample (FIG. 12). In some embodiments, the water sample and hydrophobic DES are mixed for a period of interaction sufficient to extract at least 40% of plastic contaminants from the water sample (FIG. 12). In some embodiments, the water sample and hydrophobic DES are mixed for a period of interaction sufficient to extract at least 50% of plastic contaminants from the water sample (FIG. 12). In some embodiments, the water sample and hydrophobic DES are mixed for a period of interaction sufficient to extract at least 60% of plastic contaminants from the water sample (FIG. 12). In some embodiments, the water sample and hydrophobic DES are mixed for a period of interaction sufficient to extract at least 70% of plastic contaminants from the water sample (FIG. 12). In some embodiments, the water sample and hydrophobic DES are mixed for a period of interaction sufficient to extract at least 80% of plastic contaminants from the water sample (FIG. 12). In some embodiments, the water sample and hydrophobic DES are mixed for a period of interaction sufficient to extract at least 90% of plastic contaminants from the water sample (FIG. 12).

Following phase separation of the hydrophobic DES and the aqueous portion of the mixture, in some embodiments, the enriched hydrophobic DES phase may be removed from the mixture for subsequent examination.

As evidenced above, in some implementations, the methods of the present disclosure include applying the hydrophobic DES composition described herein directly in a two-phase system so that plastic contaminants are extracted from an aqueous phase and recovered in the hydrophobic DES phase. It should be appreciated, however, that although interaction of the hydrophobic DES and the water sample within the methods described herein is primarily referred to as being facilitated by mixing the hydrophobic DES and water sample together to form a mixture, alternative means of hydrophobic DES and water sample interaction are also contemplated. For example, in one alternative embodiment, the hydrophobic DES may be immobilized on a support, such as a membrane or porous medium, so that plastic contaminants in a water sample are extracted from the water sample as the water sample passes through the support on which the hydrophobic DES is disposed. In another alternative embodiment, the plastic contaminant detection and extraction methods may include cross-linking the hydrophobic DES to form a polymeric hydrophobic DES structure and then mixing the polymeric hydrophobic DES structure with a contaminated water sample including plastic contaminants.

The hydrophobic DES utilized in the methods of the present disclosure includes a hydrogen bond acceptor (HBA) and a hydrogen bond donor (HBD).

Figure 2A:
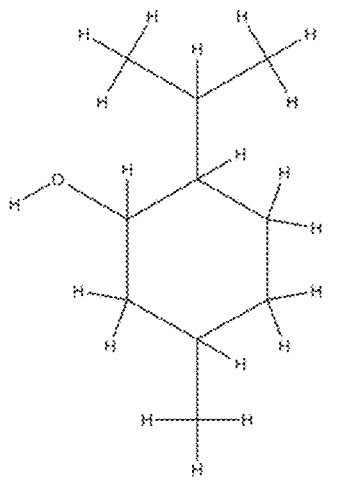
FIGS. 2A-2D show the chemical structures of the organic molecules used in the synthesis of the hydrophobic DES compositions of FIG. 1. (A) Chemical structure of decanoic acid (Dea). (B) Chemical structure of thymol (Thy). (C) Chemical structure of menthol (Men). (D) Chemical structure of lidocaine (Lid).
Figures 2B, 2C:
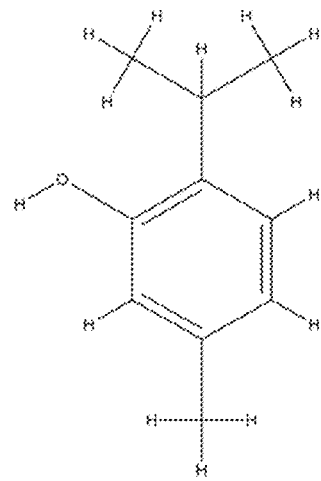

In some embodiments, the hydrophobic DES includes a HBA selected from one of: menthol (FIGS. 1 and 2C); thymol (FIGS. 1 and 2B); and decanoic acid (FIGS. 1 and 2A). Although the HBA of the hydrophobic DES is primarily referred to herein as being menthol, thymol, or decanoic acid, without wishing to be bound by theory, it is contemplated that the HBA may alternatively be selected from one of: methyltrioctylammonium bromide; methyltrioctylammonium chloride; tetrabutylammonium bromide; tetrabutylammonium chloride; tetraheptylammonium chloride; tetraoctylammonium chloride; tetraoctylammonium bromide; dodecanoate sodium salt; and lauric acid due to such HBAs low solubility in water. It is further contemplated that, in some alternative embodiments the HBA may comprise multiple HBAs.

Figure 2D:
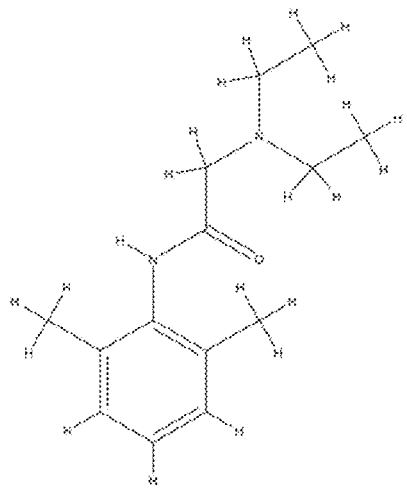

In some embodiments, the hydrophobic DES includes a HBD selected from one of: menthol (FIGS. 1 and 2C) and lidocaine (FIG. 1 and FIG. 2D). Although the HBD of the hydrophobic DES is primarily referred to herein as being menthol or lidocaine, without wishing to be bound by any particular theory, it is contemplated that the HBD may alternatively be selected from one of: acetic acid; acrylic acid; butyric acid; hexanoic acid; hexadecanol; octanoic acid; oleic acid; decanoic acid; decyl alcohol; dodecyl alcohol; lauric acid; lactic acid; levulinic acid; palmitic acid; propionic acid; pyruvic acid; phenylacetic acid; myristic acid; mandelic acid; nonanoic acid; cis-9-octadecenoic acid; ricinoleic acid; ethylene glycol; 1-propanol; 1,3-propanediol; glycerol; 1-butanol; 1,2-butanediol; 1-tetradecanol; hexyl alcohol; capryl alcohol; cyclohexanol; camphor; ibuprofen; ibuprofen acid; perfluorodecanoic acid; stearic acid; and undecylenic acid. It is further contemplated that, in some alternative embodiments the HBD may comprise multiple HBDs.

In some embodiments, the hydrophobic DES is synthesized by mixing the HBA and the HBD at a molar ratio ranging from about 0.1 to about 10 of HBA to about 1 of HBD. Following mixture of the HBA and HBD, the eutectic mixture is preferably heated and constantly stirred until a homogenous transparent liquid is obtained. In some embodiments, heating of the eutectic mixture occurs at temperatures of about 60° C.

The HBA and HBD selected for use in the synthesis of the hydrophobic DES and molar ratios corresponding to the same can be selected and modified to extract specific substrates within a contaminated water sample. In this regard a variety of different hydrophobic DESs may be utilized in the methods of the present disclosure. For example, in some embodiments, the hydrophobic DES may comprise decanoic acid and menthol mixed at a molar ratio of about 1:1 (FIG. 1) to extract PET-based plastic contaminants. In another embodiment, the hydrophobic DES may comprise decanoic acid and menthol mixed at a molar ratio of about 1:2 (FIG. 1). In another embodiment, the hydrophobic DES may comprise decanoic acid and lidocaine mixed at a molar ratio of about 2:1 (FIG. 1). In another embodiment, the hydrophobic DES may comprise menthol and lidocaine mixed at a molar ratio of about 2:1 (FIG. 1). In another embodiment, the hydrophobic DES may comprise thymol and lidocaine mixed at a molar ratio of about 2:1 (FIG. 1). In another embodiment, the hydrophobic DES may comprise thymol and menthol mixed at a molar ratio of about 1:1 (FIG. 1). In another embodiment, the hydrophobic DES may comprise thymol and lidocaine mixed at a molar ratio of about 1:1 (FIG. 1). In another embodiment, the hydrophobic DES may comprise thymol and menthol mixed at a molar ratio of about 1:2 (FIG. 1). Accordingly, in another aspect, the presently-disclosed subject matter also includes hydrophobic DES compositions, which may be utilized in the plastic contaminant detection and extraction methods disclosed herein.

Figure 3:
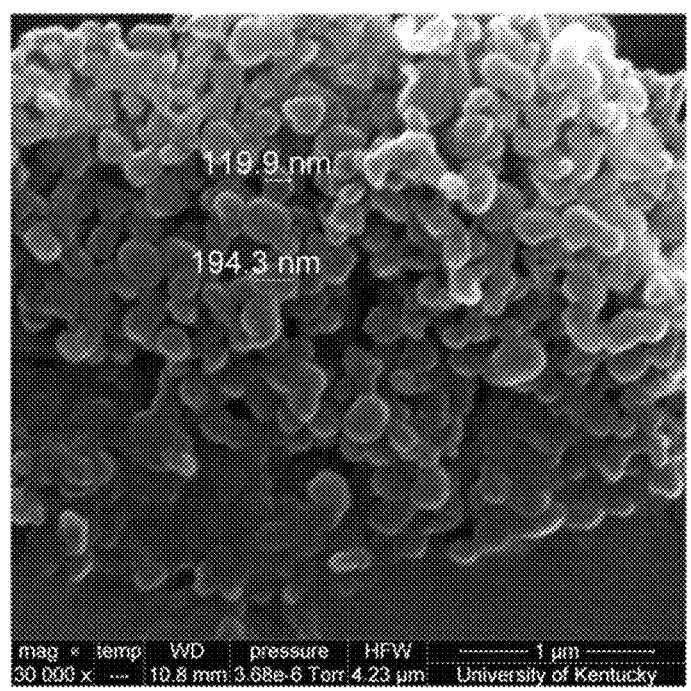
FIG. 3 is a scanning electron microscope (SEM) image of synthetic polyethylene terephthalate (PET) nanoplastic particles, a contamination commonly found in freshwater water bodies.

As a result of the affinity of the hydrophobic DES to certain organic compounds, the hydrophobic DESs and methods disclosed herein may prove useful in the extraction of a variety of plastic contaminants of different types and sizes. For example, in some implementations, the water sample in the above-described method may include nanoplastic and/or microplastic contaminants. In some embodiments, the water sample in the above-described plastic contaminant detection and extraction methods may include PET plastic particles (FIG. 3). In some embodiments, the water sample may include polystyrene (PS) plastic particles. In some embodiments, the water sample may include polypropylene (PP) plastic particles. In some embodiments, the water sample may include polyethylene (PE) plastic particles. In some embodiments, the water sample may include polylactic acid (PLA) plastic particles. In some embodiments, the water sample may include polybutylene succinate (PBS) plastic particles. In some embodiments, the water sample may include polyhydroxyalkanoate (PHA) plastic particles. In some embodiments, the water sample may include a mixture of PET and/or PS and/or PP and/or PE and/or PLA and/or PBS and/or PHA plastic particles.

Although discussed herein with respect to a "water sample," one of ordinary skill in the art will appreciate that application and use of the compositions and methods described herein are not bound to any particular volume of water. As such, the compositions and methods described herein may prove useful in the extraction of plastic contaminants from small volumes of contaminated water, such as that contained within a personal drinking container, to large volumes of contaminated water, such as lakes or rivers, alike.

Unless defined otherwise, all technical and scientific terms used herein have the same meaning as commonly understood by one of ordinary skill in the art to which the disclosure belongs. Any methods and materials similar to or equivalent to those described herein can be used in the practice or testing of the present disclosure.

As used herein, and unless otherwise indicated, the term "water sample" is understood to mean a sample which includes water of any type which is or may become contaminated by plastic contaminants, such as nanoplastics or microplastics. Accordingly, unless indicated to the contrary, "water sample" encompasses variations including: in some embodiments, the water sample includes freshwater; in some embodiments, the water sample includes brackish water; in some embodiments the water sample includes salty water, such as seawater; and in some embodiments, the water sample includes wastewater, such as from a municipal sewage or other industrial system.

Following long-standing patent law convention, the terms "a," "an," and "the" refer to "one or more" when used in this application, including the claims. Thus, for example, reference to "a cell" includes a plurality of cells, and so forth.

The terms "comprising," "including," "having," and grammatical variations thereof are intended to be inclusive and mean that there may be additional elements other than the listed elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration, percentage, or the like is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

All combinations of method or process steps as used herein can be performed in any order, unless otherwise specified or clearly implied to the contrary by the context in which the referenced combination is made.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used herein, the terms "optional" or "optionally" means that the subsequently described event or circumstance can or cannot occur, and that the description includes instances where said event or circumstance occurs and instances where it does not.

The presently-disclosed subject matter is further illustrated by the following specific but non-limiting examples. The following examples may include compilations of data that are representative of data gathered at various times during the course of development and experimentation related to the presently-disclosed subject matter. Those skilled in the art will recognize, or be able to ascertain, using no more than routine experimentation, numerous equivalents to the specific substances and procedures described herein.

EXAMPLES

The following examples focus on the discovery that certain hydrophobic DESs, in addition to their aversion to water, also exhibit an affinity towards plastic particles commonly found in contaminated water. In light of the foregoing, the inventors of the present disclosure have found that hydrophobic DESs synthesized from the mixture of certain organic molecules can be utilized in combination with contaminated water samples to effectively detect and extract plastic contaminants. In particular, the following examples show that that hydrophobic DESs synthesized from the mixture of either decanoic acid and menthol or thymol and menthol can be mixed with a contaminated water sample to detect and extract nanoplastics therefrom. The examples further show that such hydrophobic DESs do not pose a risk of further contaminating the water sample in which they are introduced and exhibit a strong affinity to PET-based plastics. Based on the foregoing, it is thus believed the methods and hydrophobic DES compositions of the present disclosure are effective tools which can be utilized in a variety of environments and water purification applications in which plastic contaminant detection or extraction is desired.

Example 1

Materials and Methods
Water Sample Preparation

Contaminated water samples including both freshwater and salty water were prepared. PET pellets were first dissolved in phenol with gentle mixing and heating at ~60° C. PET phenol solution was then gradually added drop by drop into ethanol at agitation of 600 RPM. By adjusting the agitation speed, particles with different sizes can be generated. The nanoplastic solution was centrifuged and resuspended in freshwater and salty water (3.5 wt % NaCl to mimic seawater). As shown in FIG. 3, the resulting nanoplastic particles resuspended in freshwater were generally spherical with size distribution in a range of ~119±22 nm as measured by dynamic laser scattering (DLS). Some larger nanoplastic particles with a size of ~194 nm constituting potential outliers were also observed. Interestingly, upon resuspending in salty water (3.5 wt. % NaCl), the nanoplastics tended to aggregate into much large clusters with irregular shapes of sizes in a range of 600-1000 nm. Zeta potential of PET nanoparticles decreased from −41.4±4.9 to 11.7±3.1 in freshwater and salty water, respectively, suggesting that PET nanoparticles tend to aggregate at a high ionic salt solution.

Synthesis of Hydrophobic DESs

A first hydrophobic DES was synthesized by mixing decanoic acid and menthol at a 1:1 molar ratio (Dea:Men (1:1) DES). A second hydrophobic DES was synthesized by mixing thymol and menthol at a 1:1 molar ratio (Thy:Men (1:1) DES). Both the first and second hydrophobic DESs appeared to be colorless, transparent liquids with densities slightly less than the density of water. Each eutectic mixture was followed by heating to 60° C. with a constant stirring until a homogenous and transparent liquid was obtained.

Mixture of Water Sample and Hydrophobic DES

Figures 7, 8:
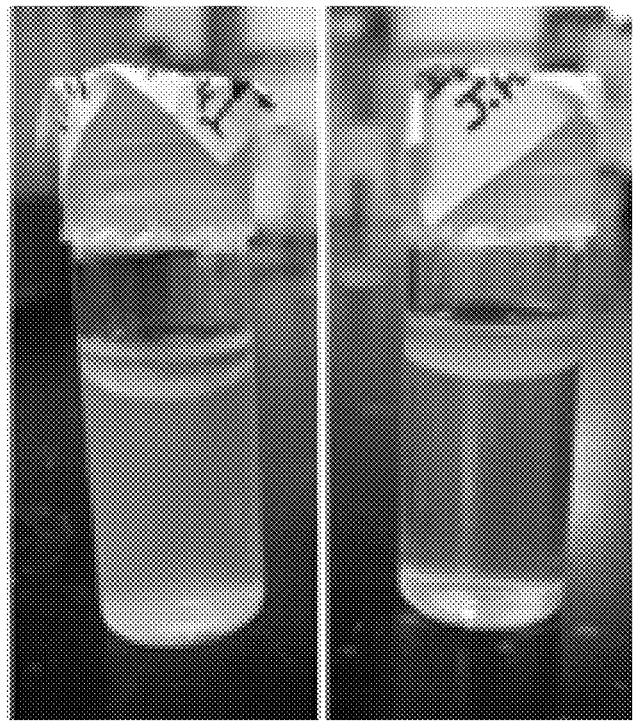
FIG. 7 is an image of a mixture (10:1 v/v) of a freshwater water sample contaminated with PET nanoplastic particles (bottom layer) and Dea:Men (1:1) DES after phase separation (top layer).
FIG. 8 is an image of a mixture (10:1 v/v) of a salty water (3.5 wt % NaCl) water sample contaminated with PET nanoplastic particles (bottom layer) and Dea:Men (1:1) DES after phase separation (top layer).

A total of four test samples were prepared for nanoplastic extraction testing by combining the two hydrophobic DESs (i.e., Dea:Men (1:1) DES and Thy:Men (1:1) DES) with either contaminated freshwater or contaminated salty water in different volume to volume ratios (v/v). Specifically, a first sample was prepared by combining Dea:Men (1:1) DES and contaminated freshwater at a 1:1 v/v (FIGS. 5B (pre-mixing), 5C (post-mixing, pre-phase separation), and 5D (post-phase separation)), a second sample was prepared by combining Thy:Men (1:1) DES and contaminated freshwater at a 1:1 v/v (FIGS. 6A (post-mixing, pre-phase separation), 6B (post-phase separation)), a third sample was prepared by combining Dea:Men (1:1) with contaminated freshwater at a 1:10 v/v (FIG. 7), and a fourth sample was prepared by combining Dea:Men (1:1) with contaminated salty water at a 1:10 v/v (FIG. 8). Each hydrophobic DES initially formed a clear layer on top of the contaminated water sample with which it was combined (as shown, e.g., in FIG. 5B). Following the initial combination of hydrophobic DES and contaminated water sample (as shown, e.g., in FIGS. 5C and 6A), each mixture was allowed to either sit or was centrifuged at 1,000 rpm for two minutes for phase separation (as shown in FIGS. 5D, 6B, 7, and 8).

Water Repulsion and DES Affinity to PET

The water-repellent property of PET and the affinity between PET and DESs were characterized by measuring the static contact angle, which is determined between a liquid droplet and a surface. Generally, a solid surface is considered as hydrophobic if its contact angle against water is larger than 90°.

Free Energy of PET from Aqueous to DES Phase

Figure 10:
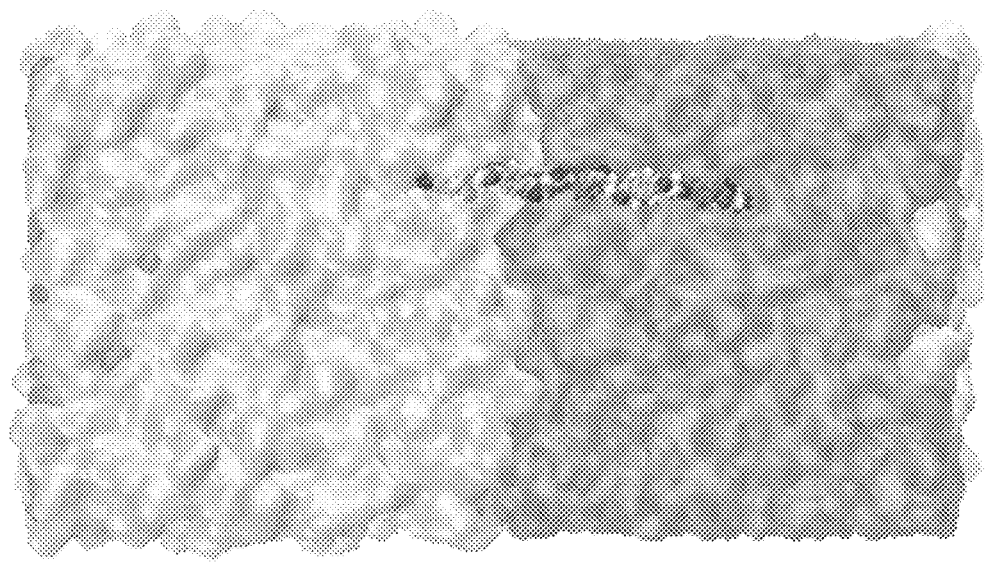
FIG. 10 is a snapshot of a metadynamic simulation system with a PET 5-monomer chain (VDW mode) in a hydrophobic DES comprising thymol and menthol in a 2:1 molar ratio (Thy:Men (2:1)) and freshwater interface.

The free energy profile for transferring a PET 5-monomer chain from the water phase to a hydrophobic DES synthesized from thymol and menthol at a molar ratio of 2:1 (Thy:Men (2:1) DES) using well-tempered metadynamics simulations was also explored. The simulation system was built by placing the PET chain in the water phase. FIG. 10 shows a snapshot of the initial configuration for the simulation system. The position of the center of mass of the PET chain was used as the collective variable in the well-tempered metadynamics. The whole simulation was conducted using Groningen Machine for Chemical Simulations (GROMACS) and PLUMED-implemented GROMACS.

Results and Discussion

Nanoplastic Extraction from Contaminated Water Samples

Figure 4A:
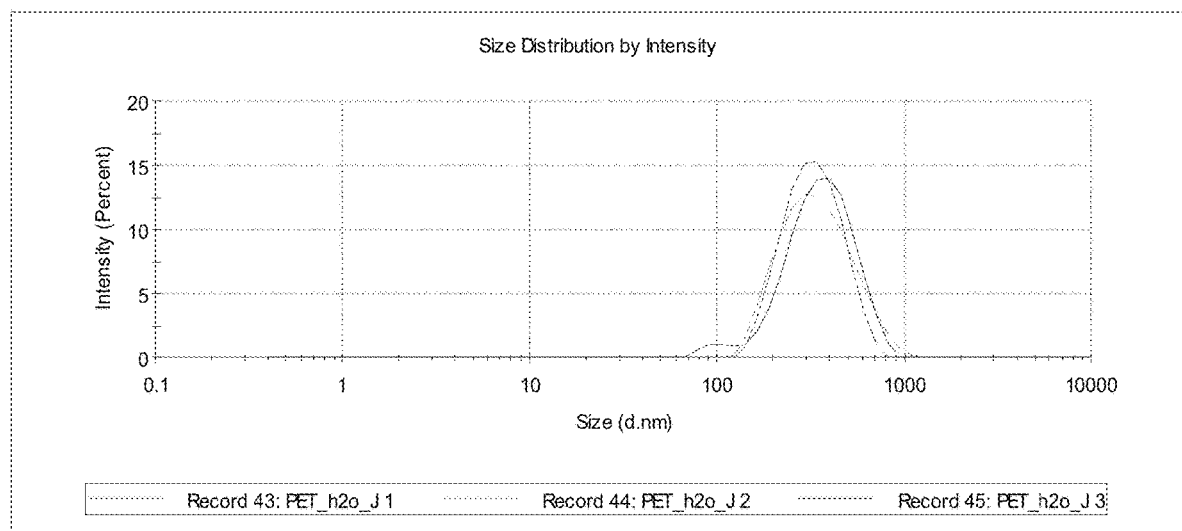
FIGS. 4A-4B are graphs showing the particle size distribution of synthetic PET nanoplastic particles in (A) a contaminated freshwater water sample and (B) a contaminated salty water (3.5 wt % NaCl) water sample, as measured by dynamic laser scattering (DLS).
Figure 4B:
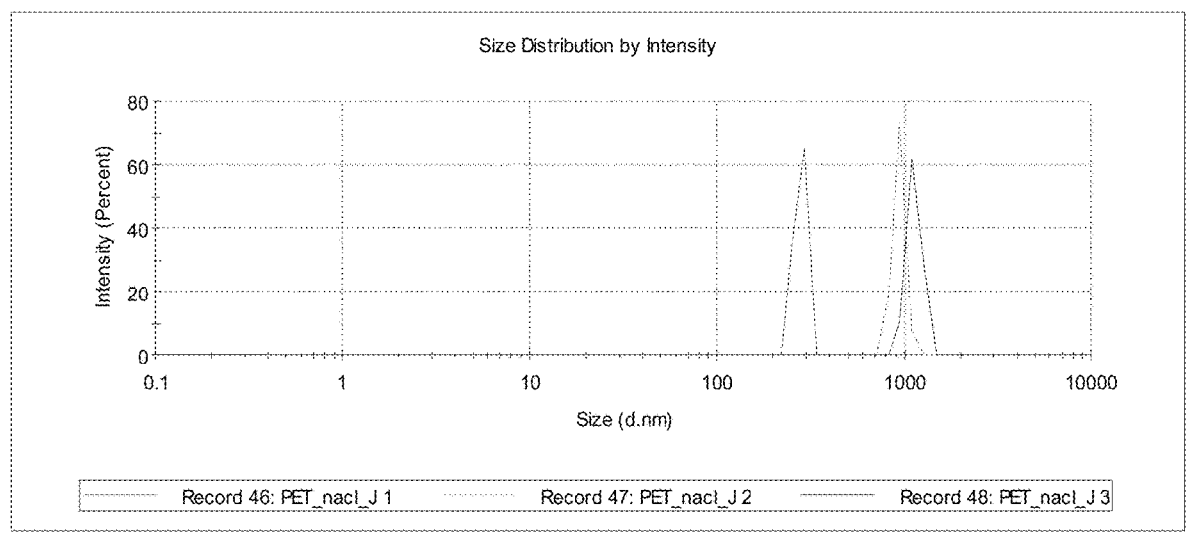

Nanoplastic extraction was observed in the DES phase (i.e., the portion of the mixture containing the hydrophobic DES and floating above the aqueous portion of the mixture) of each sample tested. As such, the nanoplastics observed within the DES phase of the samples shown in FIGS. 5D, 6B, 7, and 8 thus evidence that both Dea:Men (1:1) DES and Thy:Men (1:1) DES are hydrophobic DESs capable of extracting nanoplastic particles from contaminated water samples. It was observed that the plastic particles were evenly distributed in the DES phase of the sample including Dea:Men (1:1) mixed with contaminated freshwater at a 1:1 v/v (FIG. 5D), whereas the nanoplastics extracted in the sample including Thy:Men (1:1) mixed with contaminated freshwater at a 1:1 v/v tended to stay in the water/DES interface (FIG. 6B). It was also observed that greater nanoplastic extraction occurred in the sample including Dea:Men (1:1) mixed with contaminated salty water at a 1:10 v/v (FIG. 8) than the sample including Dea:Men (1:1) mixed with contaminated freshwater at a 1:10 v/v (FIG. 7). The tendency of nanoplastics to aggregate in clusters of larger particle size in salty water as compared to freshwater (FIG. 4) appears to facilitate greater plastic contaminant extraction and presence within the hydrophobic DES phase.

Water Repulsion and DES Affinity to PET

Figure 9:
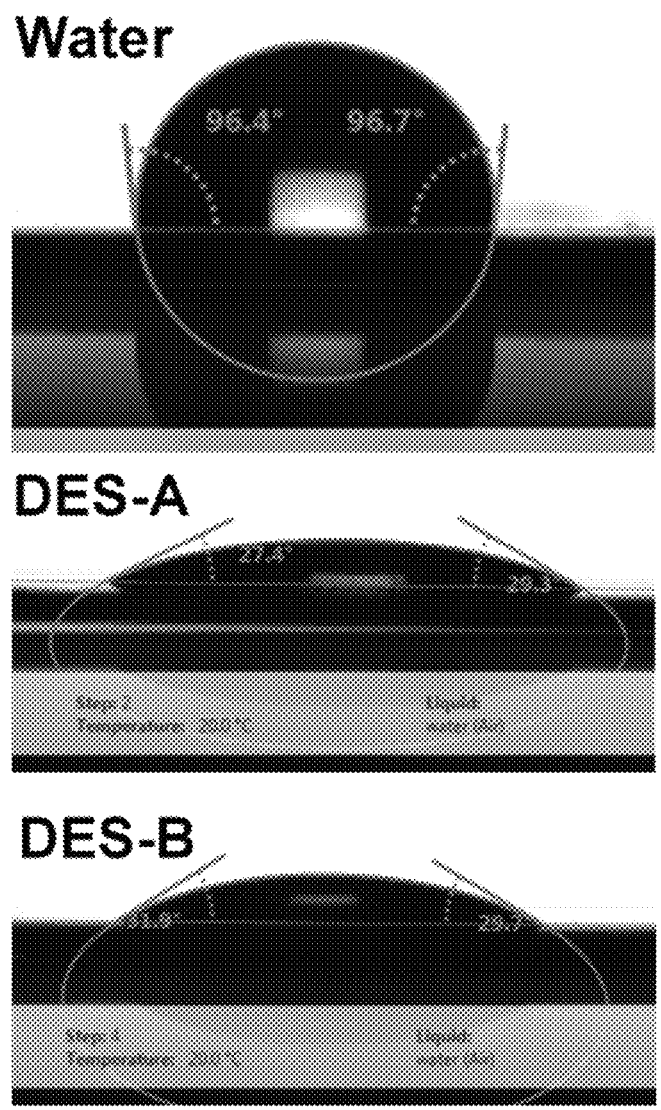
FIG. 9 is an image showing the different contact angles exhibited by freshwater, Dea:Men (1:1) DES, and Thy:Men (1:1) DES on a PET film.

FIG. 9 shows the contact angles of freshwater (indicated with the label "Water") and the hydrophobic DES of Dea:Men (1:1) (indicated with label "DES-A") and the hydrophobic DES of Thy:Men (1:1) (indicated with label "DES-B") toward PET. When dropping 10$\mu$l of freshwater onto a flat PET film, the contact angle was around 95.52±1.55°, which indicates a hydrophobic surface. But when dropping the same amount of DES solvents onto the PET film, the contact angle significantly declined to around 28.35±1.34° for Dea:Men (1:1) DES and to around 30.80±1.56 for Thy:Men (1:1) DES, suggesting a strong affinity between PET and the DES solvents of Dea:Men (1:1) DES and Thy:Men (1:1) DES.

Free Energy of PET from Aqueous to DES Phase

Figure 11:
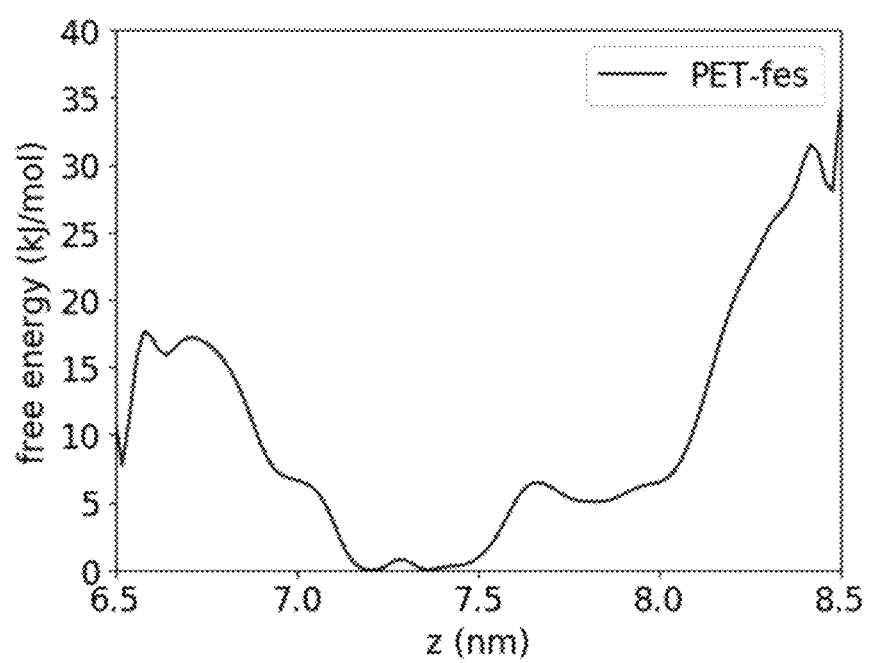
FIG. 11 is a graph showing the free energy profile of the PET 5-monomer chain around the Thy:Men (2:1) DES-freshwater interface of FIG. 10.

The free energy profile confirms that the interface plays an important role in the distribution of PET chains in the DES-water sample systems. FIG. 11 shows the free energy profile as a function of the position of the center of mass of PET chain around the interface in the DES-water system. The fluctuation of the free energy profile shows that distribution of the PET chains varies as a function of their distance to the interface.

Example 2

Materials and Methods

The plastic contaminant extraction efficiency within a freshwater sample contaminated by PET was measured for three different hydrophobic DESs: (i) Dea:Men (1:1); (ii) Dea:Men (1:2); and (iii) Thy:Men (1:1).

The contaminated water sample in which each hydrophobic DES was implemented contained 1 mg/ml PET nanoplastics, a concentration much higher than the concentration typically found in environmental samples. Each contaminated water sample was prepared using PET pellets in the same manner and using the same methods as described above in Example 1.

The first hydrophobic DES was synthesized by mixing decanoic acid and menthol at a 1:1 molar ratio, the second hydrophobic DES was synthesized by mixing decanoic acid and menthol at a 1:2 molar ratio, and the third hydrophobic DES was synthesized by mixing thymol with menthol at a 1:1 molar ratio. Each eutectic mixture was followed by heating to 60° C. with a constant stirring until a homogenous and transparent liquid was obtained.

A total of three samples were prepared for by mixing each of the three hydrophobic DESs (Dea:Men (1:1); Dea:Men (1:2); and Thy:Men (1:1)) with the contaminated water sample at a 1:1 v/v. Following the initial combination of the hydrophobic DES and contaminated water sample, each mixture was constantly stirred for 32 hours. Over the course of the 32-hour period, the percentage of PET plastic contaminants extracted from each water sample was measured by optical density reading at 600 nm in the aqueous portion of the mixture.

Results and Discussion

The extraction efficiency of the hydrophobic DESs across the three samples ranged from 87% to 91%. Specifically, it was found that the sample with Dea:Men (1:1) plateaued at 90% of PET extracted, the sample with Dea:Men (1:2) plateaued at 91% of PET extracted, and Thy:Men (1:1) plateaued at 87% of PET extracted (FIG. 12).

All publications, patents, and patent applications mentioned in this specification are herein incorporated by reference to the same extent as if each individual publication, patent, or patent application was specifically and individually indicated to be incorporated by reference, including the references set forth in the following references list:

REFERENCES

1. Barnes, D. K. A., Invasions by marine life on plastic debris. *Nature* 2002, 416 (6883), 808-809.
2. Mason, S. A.; Kammin, L.; Eriksen, M.; Aleid, G.; Wilson, S.; Box, C.; Williamson, N.; Riley, A., Pelagic plastic pollution within the surface waters of Lake Michigan, USA. *Journal of Great Lakes Research* 2016, 42 (4), 753-759.
3. Wilcox, C.; Van Sebille, E.; Hardesty, B. D., Threat of plastic pollution to seabirds is global, pervasive, and increasing. *Proceedings of the National Academy of Sciences* 2015, 112 (38), 11899-11904.
4. Cózar, A.; Echevarria, F.; González-Gordillo, J. I.; Irigoien, X.; Úbeda, B.; Hernandez-León, S.; Palma, Á. T.; Navarro, S.; García-de-Lomas, J.; Ruiz, A.; Fernández-de-Puelles, M. L.; Duarte, C. M., Plastic debris in the open ocean. *Proceedings of the National Academy of Sciences* 2014, 111 (28), 10239-10244.
5. Borrelle, S. B.; Rochman, C. M.; Liboiron, M.; Bond, A. L.; Lusher, A.; Bradshaw, H.; Provencher, J. F., Opinion: Why we need an international agreement on marine plastic pollution. *Proceedings of the National Academy of Sciences* 2017, 114 (38), 9994-9997.

6. Gibb, B. C., Plastics are forever. *Nature Chemistry* 2019, 11 (5), 394-395.
7. Eriksen, M.; Lebreton, L. C. M.; Carson, H. S.; Thiel, M.; Moore, C. J.; Borerro, J. C.; Galgani, F.; Ryan, P. G.; Reisser, J., Plastic Pollution in the World's Oceans: More than 5 Trillion Plastic Pieces Weighing over 250,000 Tons Afloat at Sea. *PLOS ONE* 2014, 9 (12), e111913.
8. Geyer, R.; Jambeck, J. R.; Law, K. L., Production, use, and fate of all plastics ever made. *Science Advances* 2017, 3 (7), e1700782.
9. Ng, E.-L.; Huerta Lwanga, E.; Eldridge, S. M.; Johnston, P.; Hu, H.-W.; Geissen, V.; Chen, D., An overview of microplastic and nanoplastic pollution in agroecosystems. *Science of The Total Environment* 2018, 627, 1377-1388.
10. Cortés, C.; Domenech, J.; Salazar, M.; Pastor, S.; Marcos, R.; Hernández, A., Nanoplastics as a potential environmental health factor: effects of polystyrene nanoparticles on human intestinal epithelial Caco-2 cells. *Environmental Science: Nano* 2020.
11. Revel, M.; Châtel, A.; Mouneyrac, C., Micro(nano) plastics: A threat to human health? *Current Opinion in Environmental Science & Health* 2018, 1, 17-23.
12. Mattsson, K.; Jocic, S.; Doverbratt, I.; Hansson, L.-A., Chapter 13—Nanoplastics in the Aquatic Environment. In *Microplastic Contamination in Aquatic Environments*, Zeng, E. Y., Ed. Elsevier: 2018; pp 379-399.
13. Gigault, J.; Halle, A. t.; Baudrimont, M.; Pascal, P.-Y.; Gauffre, F.; Phi, T.-L.; El Hadri, H.; Grassl, B.; Reynaud, S., Current opinion: What is a nanoplastic? *Environmental Pollution* 2018, 235, 1030-1034.
14. Hernandez, L. M.; Yousefi, N.; Tufenkji, N., Are There Nanoplastics in Your Personal Care Products? *Environmental Science & Technology Letters* 2017, 4 (7), 280-285.
15. da Costa, J. P.; Santos, P. S. M.; Duarte, A. C.; Rocha-Santos, T., (Nano)plastics in the environment—Sources, fates and effects. *Science of The Total Environment* 2016, 566-567, 15-26.
16. Koelmans, A. A., Proxies for nanoplastic. *Nature Nanotechnology* 2019, 14 (4), 307-308.
17. Wagner, S.; Reemtsma, T., Things we know and don't know about nanoplastic in the environment. *Nature Nanotechnology* 2019, 14 (4), 300-301.
18. Ter Halle, A.; Jeanneau, L.; Martignac, M.; Jardé, E.; Pedrono, B.; Brach, L.; Gigault, J., Nanoplastic in the North Atlantic Subtropical Gyre. *Environmental Science & Technology* 2017, 51 (23), 13689-13697.
19. Alimi, O. S.; Farner Budarz, J.; Hernandez, L. M.; Tufenkji, N., Microplastics and Nanoplastics in Aquatic Environments: Aggregation, Deposition, and Enhanced Contaminant Transport. *Environmental Science & Technology* 2018, 52 (4), 1704-1724.
20. Shen, M.; Zhang, Y.; Zhu, Y.; Song, B.; Zeng, G.; Hu, D.; Wen, X.; Ren, X., Recent advances in toxicological research of nanoplastics in the environment: A review. *Environmental Pollution* 2019, 252, 511-521.
21. Nguyen, B.; Claveau-Mallet, D.; Hernandez, L. M.; Xu, E. G.; Farner, J. M.; Tufenkji, N., Separation and Analysis of Microplastics and Nanoplastics in Complex Environmental Samples. *Accounts of Chemical Research* 2019, 52 (4), 858-866.
22. Heddagaard, F. E.; Møller, P., Hazard assessment of small-size plastic particles: is the conceptual framework of particle toxicology useful? *Food and Chemical Toxicology* 2019, 111106.
23. Mao, Y.; Li, H.; Huangfu, X.; Liu, Y.; He, Q., Nanoplastics display strong stability in aqueous environments: Insights from aggregation behaviour and theoretical calculations. *Environmental Pollution* 2020, 258, 113760.
24. van Osch, D. J. G. P.; Zubeir, L. F.; van den Bruinhorst, A.; Rocha, M. A. A.; Kroon, M. C., Hydrophobic deep eutectic solvents as water-immiscible extractants. *Green Chemistry* 2015, 17 (9), 4518-4521.
25. Zhang, Q.; De Oliveira Vigier, K.; Royer, S.; Jerome, F., Deep eutectic solvents: syntheses, properties and applications. *Chemical Society Reviews* 2012, 41 (21), 7108-7146.
26. Liu, Y.; Friesen, J. B.; McAlpine, J. B.; Lankin, D. C.; Chen, S.-N.; Pauli, G. F., Natural Deep Eutectic Solvents: Properties, Applications, and Perspectives. *Journal of Natural Products* 2018, 81 (3), 679-690.
27. Florindo, C.; Branco, L. C.; Marrucho, I. M., Development of hydrophobic deep eutectic solvents for extraction of pesticides from aqueous environments. *Fluid Phase Equilibria* 2017, 448, 135-142.
28. Cao, J.; Yang, M.; Cao, F.; Wang, J.; Su, E., Well-Designed Hydrophobic Deep Eutectic Solvents As Green and Efficient Media for the Extraction of Artemisinin from *Artemisia annua* Leaves. *ACS Sustainable Chemistry & Engineering* 2017, 5 (4), 3270-3278.
29. van Osch, D. J. G. P.; Dietz, C. H. J. T.; van Spronsen, J.; Kroon, M. C.; Gallucci, F.; van Sint Annaland, M.; Tuinier, R., A Search for Natural Hydrophobic Deep Eutectic Solvents Based on Natural Components. *ACS Sustainable Chemistry & Engineering* 2019, 7 (3), 2933-2942.
30. Ferreira, I.; Venancio, C.; Lopes, I.; Oliveira, M., Nanoplastics and marine organisms: What has been studied? *Environmental Toxicology and Pharmacology* 2019, 67, 1-7.
31. Mintenig, S. M.; Bauerlein, P. S.; Koelmans, A. A.; Dekker, S. C.; van Wezel, A. P., Closing the gap between small and smaller: towards a framework to analyse nano- and microplastics in aqueous environmental samples. *Environmental Science: Nano* 2018, 5 (7), 1640-1649.
32. Lambert, S.; Wagner, M., Characterisation of nanoplastics during the degradation of polystyrene. *Chemosphere* 2016, 145, 265-268.
33. Dawson, A. L.; Kawaguchi, S.; King, C. K.; Townsend, K. A.; King, R.; Huston, W. M.; Bengtson Nash, S. M., Turning microplastics into nanoplastics through digestive fragmentation by Antarctic krill. *Nature Communications* 2018, 9 (1), 1001.
34. Ekvall, M. T.; Lundqvist, M.; Kelpsiene, E.; Šileikis, E.; Gunnarsson, S. B.; Cedervall, T., Nanoplastics formed during the mechanical breakdown of daily-use polystyrene products. *Nanoscale Advances* 2019, 1 (3), 1055-1061.
35. Enfrin, M.; Lee, J.; Gibert, Y.; Basheer, F.; Kong, L.; Dumée, L. F., Release of hazardous nanoplastic contaminants due to microplastics fragmentation under shear stress forces. *Journal of Hazardous Materials* 2020, 384, 121393.
36. Hollóczki, O.; Gehrke, S., Can Nanoplastics Alter Cell Membranes? *ChemPhysChem* n/a (n/a).
37. Bergami, E.; Pugnalini, S.; Vannuccini, M. L.; Manfra, L.; Faleri, C.; Savorelli, F.; Dawson, K. A.; Corsi, I., Long-term toxicity of surface-charged polystyrene nanoplastics to marine planktonic species *Dunaliella tertiolecta* and Artemia franciscana. *Aquatic Toxicology* 2017, 189, 159-169.
38. Tallec, K.; Huvet, A.; Di Poi, C.; Gonzalez-Fernández, C.; Lambert, C.; Petton, B.; Le Goïc, N.; Berchel, M.; Soudant, P.; Paul-Pont, I., Nanoplastics impaired oyster free living stages, gametes and embryos. *Environmental Pollution* 2018, 242, 1226-1235.
39. Sendra, M.; Saco, A.; Yeste, M. P.; Romero, A.; Novoa, B.; Figueras, A., Nanoplastics: From tissue accumulation to cell translocation into Mytilus galloprovincialis hemocytes. resilience of immune cells exposed to nanoplastics and nanoplastics plus *Vibrio* splendidus combination. *Journal of Hazardous Materials* 2019, 121788.
40. Abraham, M. J.; Murtola, T.; Schulz, R.; Páll, S.; Smith, J. C.; Hess, B.; Lindahl, E., GROMACS: High performance molecular simulations through multi-level parallelism from laptops to supercomputers. *SoftwareX* 2015, 1-2, 19-25.
41. Luzar, A.; Chandler, D., Hydrogen-bond kinetics in liquid water. *Nature* 1996, 379 (6560), 55-57.
42. Bonomi, M.; Bussi, G.; Camilloni, C.; Tribello, G. A.; Banáš, P.; Barducci, A.; Bernetti, M.; Bolhuis, P. G.; Bottaro, S.; Branduardi, D.; Capelli, R.; Carloni, P.; Ceriotti, M.; Cesari, A.; Chen, H.; Chen, W.; Colizzi, F.; De, S.; De La Pierre, M.; Donadio, D.; Drobot, V.; Ensing, B.; Ferguson, A. L.; Filizola, M.; Fraser, J. S.; Fu, H.; Gasparotto, P.; Gervasio, F. L.; Giberti, F.; Gil-Ley, A.; Giorgino, T.; Heller, G. T.; Hocky, G. M.; Iannuzzi, M.; Invernizzi, M.; Jelfs, K. E.; Jussupow, A.; Kirilin, E.; Laio, A.; Limongelli, V.; Lindorff-Larsen, K.; Löhr, T.; Marinelli, F.; Martin-Samos, L.; Masetti, M.; Meyer, R.; Michaelides, A.; Molteni, C.; Morishita, T.; Nava, M.; Paissoni, C.; Papaleo, E.; Parrinello, M.; Pfaendtner, J.; Piaggi, P.; Piccini, G.; Pietropaolo, A.; Pietrucci, F.; Pipolo, S.; Provasi, D.; Quigley, D.; Raiteri, P.; Raniolo, S.; Rydzewski, J.; Salvalaglio, M.; Sosso, G. C.; Spiwok, V.; Sponer, J.; Swenson, D. W. H.; Tiwary, P.; Valsson, O.; Vendruscolo, M.; Voth, G. A.; White, A.; The, P. c., Promoting transparency and reproducibility in enhanced molecular simulations. *Nature Methods* 2019, 16 (8), 670-673.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for detecting nanoplastic particles suspended within a water sample, comprising:
   introducing the water sample to a hydrophobic deep eutectic solvent; and
   examining the hydrophobic deep eutectic solvent for nanoplastic particle enrichment after a period of interaction with the water sample including quantifying a number of nanoplastic contaminants within the hydrophobic deep eutectic solvent.
2. The method according to claim 1, wherein introducing the water sample to the hydrophobic deep eutectic solvent includes mixing the water sample with the deep eutectic solvent to form a mixture, and wherein the hydrophobic deep eutectic solvent is examined for nanoplastic particle enrichment following phase separation between the hydrophobic deep eutectic solvent and an aqueous portion of the mixture.
3. The method according to claim 2, wherein the hydrophobic deep eutectic solvent and the water sample are mixed in a volume to volume ratio ranging from about 1 of hydrophobic deep eutectic solvent to 10 of water sample to about 1 of hydrophobic deep eutectic solvent to about 1 of water sample.
4. The method according to claim 1, wherein the hydrophobic deep eutectic solvent includes a hydrogen bond acceptor and a hydrogen bond donor mixed in a molar ratio of about 0.1 to about 10 of hydrogen bond acceptor to about 1 of hydrogen bond donor.
5. The method according to claim 1, wherein the hydrophobic deep eutectic solvent includes a hydrogen bond acceptor selected from one of decanoic acid and thymol.
6. The method according to claim 1, wherein the hydrophobic deep eutectic solvent includes a hydrogen bond donor selected from one of lidocaine and menthol.
7. The method according to claim 1, wherein the hydrophobic deep eutectic solvent includes decanoic acid and menthol.
8. The method according to claim 7, wherein a molar ratio of the hydrophobic deep eutectic solvent is about 1 of decanoic acid to about 1 of menthol.
9. The method according to claim 7, wherein a molar ratio of the hydrophobic deep eutectic solvent is about 1 of decanoic acid to about 2 of menthol.
10. The method according to claim 1, wherein the nanoplastic particles include polyethylene terephthalate.
11. The method according to claim 1, wherein the hydrophobic deep eutectic solvent is examined for nanoplastic particle enrichment via at least one of microscopy, spectrophotometry, and thermogravimetric analysis.
12. The method of claim 1, wherein the water sample is salty water that is at least 3.5 wt % NaCl.
13. A method for detecting plastic contaminants within a water sample, comprising:
    introducing the water sample to a hydrophobic deep eutectic solvent; and
    examining the hydrophobic deep eutectic solvent for plastic contaminant enrichment after a period of interaction with the water sample;
    wherein the hydrophobic deep eutectic solvent includes thymol and menthol.
14. The method according to claim 13, wherein a molar ratio of the hydrophobic deep eutectic solvent is about 1 of thymol to about 1 of menthol.
15. The method according to claim 13, wherein a molar ratio of the hydrophobic deep eutectic solvent is about 2 of thymol to about 1 of menthol.
16. A method for extracting nanoplastic particles suspended within a water sample, comprising:
    introducing the water sample to a hydrophobic deep eutectic solvent for a period of interaction sufficient for the hydrophobic deep eutectic solvent to extract at least some of the nanoplastic particles from the water sample; and
    quantifying a number of nanoplastic contaminants within the hydrophobic deep eutectic solvent.
17. The method according to claim 16, wherein the hydrophobic deep eutectic solvent includes (i) a hydrogen bond acceptor selected from one of decanoic acid and thymol and (ii) a hydrogen bond donor selected from one of lidocaine and menthol.
18. The method according to claim 17, wherein introducing the water sample to the hydrophobic deep eutectic solvent includes mixing the water sample with the hydrophobic deep eutectic solvent for a period of interaction sufficient to extract at least 60% of the nanoplastic particles from the water sample.
19. The method according to claim 17, wherein introducing the water sample to the hydrophobic deep eutectic solvent includes mixing the water sample with the hydrophobic deep eutectic solvent for a period of interaction sufficient to extract at least 70% of the nanoplastic particles from the water sample.

20. The method according to claim 17, wherein introducing the water sample to the hydrophobic deep eutectic solvent includes mixing the water sample with the hydrophobic deep eutectic solvent for a period of interaction sufficient to extract at least 80% of the nanoplastic particles from the water sample.

21. The method according to claim 17, wherein introducing the water sample to the hydrophobic deep eutectic solvent includes mixing the water sample with the hydrophobic deep eutectic solvent for a period of interaction sufficient to extract at least 90% of the nanoplastic particles from the water sample.

22. The method of claim 16, wherein the water sample is salty water that is at least 3.5 wt % NaCl.

* * * * *